United States Patent [19]

Austel et al.

[11] 4,299,834
[45] Nov. 10, 1981

[54] 8-PHENYL-PURINES AND PHARMACEUTICAL COMPOSITIONS CONTAINING SAME

[75] Inventors: Volkhard Austel; Eberhard Kutter, both of Biberach; Joachim Heider, Warthausen; Willi Diederen, Biberach, all of Fed. Rep. of Germany

[73] Assignee: Boehringer Ingelheim Gesellschaft mit beschränkter Haftung, Ingelheim am Rhein, Fed. Rep. of Germany

[21] Appl. No.: 166,709

[22] Filed: Jul. 8, 1980

[30] Foreign Application Priority Data

Jul. 11, 1979 [DE] Fed. Rep. of Germany ....... 2927988

[51] Int. Cl.³ .......................................... C07D 473/00
[52] U.S. Cl. .................................... 424/253; 544/264
[58] Field of Search ......................... 544/264; 424/253

[56] References Cited

U.S. PATENT DOCUMENTS 3,813,394  5/1974  Tenshu et al. ..................... 544/264

OTHER PUBLICATIONS

Chemical Abstracts, vol. 50 1956 15540a.

Primary Examiner—Nicholas S. Rizzo
Attorney, Agent, or Firm—Hammond & Littell, Weissenberger and Muserlian

[57] ABSTRACT

This invention is directed to 8-phenyl-purines of general formula

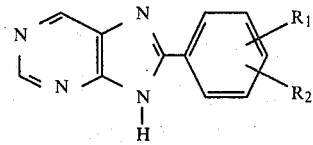

wherein
$R_1$ is a hydrogen or halogen atom; an alkoxy group optionally substituted by alkylmercapto, alkylsulfinyl or alkylsulfonyl group; or an alkylmercapto, alkylsulfinyl or alkylsulfonyl group, whereby each alkyl moiety may contain from 1 to 3 carbon atoms, and
$R_2$ is an alkoxy group with from 1 to 3 carbon atoms, and their physiologically compatible acid addition salts. The compounds exhibit valuable pharmacological properties, particularly positive inotropic activity.

10 Claims, No Drawings

8-PHENYL-PURINES AND PHARMACEUTICAL COMPOSITIONS CONTAINING SAME

This invention relates to novel 8-phenyl-purines. More particularly, this invention relates to 8-phenyl-purines of general formula

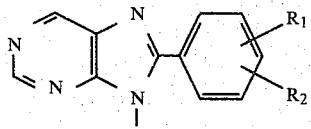
(I)

wherein
$R_1$ is a hydrogen or halogen atom; an alkoxy group of from 1 to 3 carbon atoms, the alkoxy group being optionally substituted by an alkylmercapto, alkylsulfinyl, or alkylsulfonyl group, the alkyl moiety thereof having from 1 to 3 carbon atoms; or an alkylmercapto, alkylsulfinyl, or alkylsulfonyl group, wherein the alkyl moiety has from 1 to 3 carbon atoms, and $R_2$ is an alkoxy group of from 1 to 3 carbon atoms,
and the pharmacologically acceptable acid addition salts thereof, as well as their use in pharmaceutical preparations. The 8-phenyl-purines of general Formula I exhibit valuable pharmacological properties, particularly positive inotropic activity, i.e., acting to increase muscular contractions.

In Formula I, $R_1$ may, for example, represent a hydrogen, fluorine, chlorine, or bromine atom, or a methoxy, ethoxy, propoxy, isopropoxy, methylmercapto, ethylmercapto, isopropylmercapto, methylsulfinyl, ethylsulfinyl, propylsulfinyl, methylsulfonyl, ethylsulfonyl, propylsulfonyl, isopropylsulfonyl, methylmercaptomethoxy, methylsulfinylmethoxy, methylsulfonylmethoxy, 2-methylcercaptoethoxy, 2-methylsulfinylethoxy, 2-methylsulfonylethoxy, 3-methylmercaptopropoxy, 3-methylsulfinylpropoxy, 3-methylsulfonylpropoxy, 2-ethylmercaptoethoxy, 2-ethylsulfinylethoxy, 2-ethylsulfonylethoxy, 3-ethylmercaptopropoxy, 3-ethylsulfinylpropoxy, 3-ethylsulfonylpropoxy, 2-propylmercaptoethoxy, 2-propylsulfinylethoxy, 2-propylsulfonylethoxy, 3-isopropylmercaptopropoxy, 3-isopropylsulfinylpropoxy, or 3-isopropylsulfonylpropoxy group. $R_2$ may, for example, represent a methoxy, ethoxy, propoxy, or isopropoxy group.

Preferred compounds of general Formula I are, however, those wherein
$R_1$ is a hydrogen or chlorine atom or a methoxy, methylmercapto, methylsulfinyl, methylsulfonyl, 2-methylmercaptoethoxy, or 2-methylsulfinylethoxy group, and $R_2$ is a methoxy, ethoxy, or propoxy group.
Especially preferred compounds of Formula I are those wherein $R_1$ and/or $R_2$ are in the 2-, and 3- or 4-position.

The new compounds can be obtained according to the following process:

A compound of the general formula

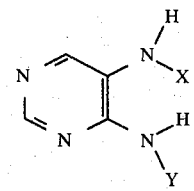
(II)

wherein
one of the radicals X and Y represents a hydrogen atom and the other of the radicals X or Y, or both of the radicals X and Y, represents a group of formula

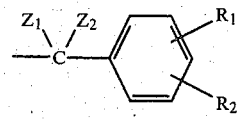

wherein
$R_1$ and $R_2$ are as defined above,
$Z_1$ and $Z_2$, which may be the same or different, each are an amino group, optionally substituted by one or two lower alkyl groups, a hydroxy group, or a mercapto group, optionally substituted by a lower alkyl group, or $Z_1$ and $Z_2$ together represent an oxygen or sulfur atom, an imino group, optionally substituted by an alkyl group of from 1 to 3 carbon atoms, or an alkylenedioxy or alkylenedithio group having 2 or 3 carbon atoms, is cyclisized, optionally in the reaction mixture.

The cyclization is conveniently carried out in a solvent such as ethanol, isopropanol, glacial acetic acid, benzene, chlorobenzene, toluene, xylene, glycol, glycolmonomethyl ether, diethyleneglycol dimethylether, dimethyl formamide, or tetraline or in an excess of the acylating agent used for the preparation of the compound of Formula II, for example, in the corresponding nitrile, anhydride, acid halogenide, ester, amide, or methoiodide. Also, the cyclization is carried out at, for example, temperatures of from about 0° to 250° C., preferably, however, at the boiling temperature of the reaction mixture, and optionally in the presence of a condensation agent such as phosphoroxy chloride, thionyl chloride, sulfonyl chloride, sulfuric acid, p-toluene sulfonic acid, hydrochloric acid, phosphoric acid, polyphosphoric acid, or acetic acid anhydride or optionally also in the presence of a base such as potassium ethylate or potassium-tert.-butylate. It is possible to carry out the cyclization without a solvent and/or without a condensation agent.

A compound of general Formula I obtained according to the invention, wherein $R_1$ contains an alkylmercapto group, can, if desired, subsequently be converted into a corresponding alkylsulfinyl compound of Formula I by means of oxidation. In addition, a compound of Formula I, wherein $R_1$ comprises an alkylmercapto or alkylsulfinyl group can be converted into a corresponding alkylsulfonyl compound of Formula I by means of oxidation.

The subsequent oxidation is preferably carried out in a solvent, for example, water, water/pyridine, ethanol, methanol, acetone, glacial acetic acid, formic acid, dilute sulfuric acid, or trifluoro acetic acid, at temperatures of from about −80° to +100° C., dependent upon the oxidation agent employed.

For the preparation of an alkylsulfinyl compound of general Formula I, the oxidation is conveniently carried out with an equivalent of the oxidizing agent used, for example, with hydrogen peroxide in glacial acetic acid, trifluoro acetic acid, or formic acid, at from about 0° to 20° C. or in acetone at from about 0° to 60° C.; with a peracid such as performic acid in glacial acetic acid or trifluoro acetic acid at from about 0° to 50° C.; with m-chloroperbenzoic acid in methylene chloride or chloroform at from about −20° to +60° C.; with sodium metaperiodate in aqueous methanol or ethanol at from about 15° to 25° C.; with N-bromo-succinimide in ethanol; with tert.-butyl-hypochlorite in methanol at from about −80° to −30° C.; with iodobenzene dichloride in aqueous pyridine at from about 0° to 50° C.; with nitric acid in glacial acetic acid at from about 0° to 20° C.; with chromic acid in glacial acetic acid or in acetone at from about 0° to 20° C.; or with sulfuryl chloride in methylene chloride at about −70° C. The thioether-chloro-complex obtained thereby is conveniently hydrolyzed with aqueous ethanol.

For the preparation of an alkylsulfonyl compound of Formula I, the oxidation is conveniently carried out with one or with two or more equivalents of the oxidizing agent used, for example, with hydrogen peroxide in glacial acetic acid, trifluoro acetic acid, or formic acid at from about 20° to 100° C. or in acetone at from about 0° to 60° C.; with a peracid such as performic acid or m-chloroperbenzoic acid in glacial acetic acid, trifluoro acetic acid, methylene chloride, or chloroform at temperatures at from about 0° to 60° C.; or with nitric acid in glacial acetic acid at from about 0° to 20° C.; with chromic acid or potassium permanganate in glacial acetic acid, aqueous sulfuric acid, or acetone at from about 0° to 20° C.

Furthermore, the resulting compounds of general Formula I can be converted, if desired, into pharmacologically acceptable salts by reaction with strong acids. Such acids may include, for example, hydrochloric acid, hydrobromic acid, sulfuric acid, and phosphoric acid.

The compounds of general Formula II used as starting materials can be obtained according to known procedures, such as, for example, by acylation of 4,5-diamino-pyrimidine.

As mentioned above, the 8-phenyl-purines of general Formula I, as well as their pharmacologically acceptable acid addition salts with strong acids, exhibit valuable pharmacological properties, particularly positive inotropic activity. To demonstrate these properties, the exemplary compounds:

A = 8-(2,4-Dimethoxy-phenyl)-purine,
B = 8-(2-Methoxy-4-methylmercapto-phenyl)-purine,
C = 8-[4-Methoxy-2-(2-methylmercapto-ethoxy)-phenyl]purine,
D = 8-[4-Methoxy-2-(2-methylsulfinyl-ethoxy)-phenyl]purine,
E = 8-(4-Methoxy-phenyl)-purine,
F = 8-(3,4-Dimethoxy-phenyl)-purine,
G = 8-(4-Chloro-2-methoxy-phenyl)-purine, and
H = 8-(2-Methoxy-4-methylsulfinyl-phenyl)-purine
were tested with regard to their biological properties in the following manner:

1. Determination of the Blood Pressure and Positive Inotropic Activity in the Cat The tests were performed in cats, which were narcotisized with pentobarbital sodium (40 mg/kg i.p.). The animals breathed spontaneously. The arterial blood pressure was measured in the aorta abdominalis by a Statham pressure transducer (P 23 Dc). The positive inotropic effect was determined by measuring the pressure in the left ventricle by means of a catheter tipmanometer (Millar PC-350 A). The contractility parameter $dp/dt_{max}$ was registered by means of an analog differentiating circuit.

The substances being tested were injected into the vena femoralis. Physiological sodium chloride solution or polydiol 200 was used as solvent. Each substance was tested in at least three cats, dose 2 mg/kg i.v. The results are set forth in the following table:

TABLE 1

| Test Compound | Dose (mg/kg i.v.) | Change of Blood Pressure (mm Hg) | Increase of $dp/dt_{max}$ (%) |
|---|---|---|---|
| A | 2.0 | + 42/31 | + 185 |
| B | 2.0 | + 27/17 | + 110 |
| C | 2.0 | + 33/20 | + 85 |
| D | 2.0 | + 28/10 | + 72 |
| E | 2.0 | − 8/7 | + 26 |
| F | 2.0 | − 18/23 | + 87 |
| G | 2.0 | − 0/11 | + 72 |
| H | 2.0 | − 8/13 | + 95 |

2. Acute Toxicity

The acute toxicity of the test compounds was determined in white mice after oral administration of a single dose of 300 mg/kg (observation time: 14 days). The results of the testing are set forth in the following table:

TABLE 2

| Test Compound | Acute Toxicity $LD_{50}$ (mg/kg p.o.) |
|---|---|
| A | >300 (0 out of 6 animals died) |
| B | >300 (2 out of 6 animals died) |
| C | >300 (0 out of 6 animals died) |
| D | >300 (0 out of 6 animals died) |
| G | >300 (1 out of 6 animals died) |
| H | ∼300 (3 out of 6 animals died) |

According to their pharmacological properties, the compounds of general Formula I prepared according to the invention, as well as their pharmacologically acceptable acid addition salts, are useful as positive inotropic agents, i.e., as stimulants to increase muscular contraction. They are especially suitable in the treatment of chronic cardiac insufficiency and cardiogenic shock.

For pharmaceutical administration, the 8-phenyl-purines of Formula I, as well as their pharmacologically acceptable acid addition salts, can be incorporated into conventional pharmaceutical preparations, such as tablets, coated tablets, powders, suppositories, suspensions, capsules, ampules, or drops. The pharmaceutical compositions may comprise one or more of the compounds of Formula I as active ingredient as well as pharmacologically acceptable carrier and/or other conventional additives and/or other active ingredients. The single dose for adults contains from about 25 to 150 mg (from about 0.35 to 2.1 mg/kg), preferably from about 50 to 100 mg (from about 0.7 to 1.4 mg/kg), of active ingredient, and the daily dose contains from about 25 to 600 mg (from about 0.35 to 9 mg/kg), preferably from about 50 to 400 mg (from about 0.7 to 5.7 mg/kg), of active ingredient.

The following examples are intended to illustrate the invention and are not to be construed as limiting the invention thereto.

EXAMPLES

Example 1

8-(2,4-Dimethoxy-phenyl)-purine

A mixture of 2 g of 4,5-diamino-pyrimidine, 4 g of 2,4-dimethoxy-benzonitrile, 6 g of p-toluene sulfonic acid hydrate, and 40 ml of benzene was heated, whereby the benzene was distilled off. The residue was heated for 30 minutes at 120° C. After cooling the residue was triturated with 2 N ammonia and extracted with ethyl acetate. The ethyl acetate phase was extracted with 2 N hydrochloric acid, the aqueous phase was neutralized and again extracted with ethyl acetate, and subsequently the organic phase was extracted with 2 N sodium hydroxide solution. When the aqueous phase was neutralized, the product was precipitated and recrystallized from water.

Yield: 0.15 g (3% of theory),
M.P.: 221° C. (decomp).

Example 2

8-(2,4-Dimethoxy-phenyl)-purine

A mixture of 5.5 g of 4,5-diaminopyrimidine and 10.9 g of 2,4-dimethoxy-benzoic acid was triturated in a mortar. The mixture was added to 100 ml of phosphorus oxychloride and refluxed for one hour. The phosphorus oxychloride was decomposed under stirring into water, and the solution obtained was neutralized with ammonia after filtration. The precipitated product was recrystallized from water and ethanol/cyclohexane (volume ratio of 1:3).

Yield: 3.5 g (27% of theory),
M.P.: 218°-220° C.

Example 3

8-(2-Methoxy-4-methylmercapto-phenyl)-purine

A mixture of 4.1 g of 4,5-diamino-pyrimidine dihydrochloride, 7.1 g of 2-methoxy-4-methylmercapto-benzoylchloride, and 50 ml of phosphorus oxychloride was refluxed for three hours. The reaction mixture was evaporated until one-half of the original volume remained, and then the remaining mixture was poured into water. The precipitate that formed was dissolved in boiling ethanol, precipitated by addition of ether, and purified by chromatography on silicagel (eluate: methylene chloride/ethanol in a volume ratio of 19:1).

Yield: 2.7 g (44% of theory),
M.p.: 212° C.

Example 4

8-[4-Methoxy-2-(2-methylmercapto-ethoxy)-phenyl]purine (a)
4,5-Bis-[4-methoxy-2-(2-methylmercapto-ethoxy)-benzoyl-amino]pyrimidine A mixture of 7 g of 4,5-diamino-pyrimidine-dihydrochloride, 26 g of 4-methoxy-2-(2-methylmercapto-ethoxy)-benzoylchloride, 150 ml of pyridine, and 2 g of 4-dimethylamino-pyridine was stirred for 20 hours at room temperature, mixed with chloroform, and washed with water. The evaporation residue of the organic phase was purified over silicagel (eluate: methylene chloride/ethanol in a volume ratio of 19:1).

Yield: 3.3 g (15% of theory),
M.p.: 139°-140° C.

(b)
8-[4-Methoxy-2-(2-methylmercapto-ethoxy)-phenyl]-purine

An amount of 3.1 g of 4,5-bis-[4-methoxy-2-(2-methylmercapto-ethoxy)-benzoylamino]pyrimidine was refluxed in 25 ml of phosphorus oxychloride for two hours. After the phosphorus oxychloride was distilled off, the residue was taken up in water and filtered, and the product was precipitated by addition of sodium bicarbonate and recrystallized from ethanol. A further fraction was obtained by purification of the mother liquors over silicagel (eluate: methylene chloride/ethanol in a volume ratio of 19:1).

Yield: 1.43 g (81% of theory),
M.p.: 173°-175° C.

Example 5

8-[4-Methoxy-2-(2-methylsulfinyl-ethoxy)-phenyl]purine

One gram of 8-[4-methoxy-2-(2-methylmercapto-ethoxy)phenyl]purine was dissolved in 10 ml of glacial acetic acid and mixed with 0.5 ml of 30% hydrogen peroxide. After standing for 3.5 hours at room temperature, the reaction mixture was diluted with water and made alkaline by means of potassium carbonate. The precipitate was recrystallized from isopropanol/ethanol in a volume ratio of 1:1.

Yield: 0.75 g (71% of theory),
M.p.: 226°-227° C.

Example 6

8-(4-Methoxy-phenyl)-purine

The above compound was prepared from 0.35 g of 4,5-bis(4-methoxybenzoylamino)-pyrimidine using a procedure analogous to that of Example 4(b).

Yield: 0.08 g (38% of theory),
M.p.: above 300° C.

Example 7

8-(4-Chloro-2-methoxy-phenyl)-purine-hydrochloride (a)
4-Amino-5-(4-chloro-2-methoxy-benzoylamino)-pyrimidine The 4-chloro-2-methoxy-benzoyl chloride prepared from 5.6 g of 4-chloro-2-methoxy-benzoic acid and 100 ml of thionyl chloride was dissolved as crude product in 100 ml of pyridine and mixed successively with 5 g of 4,5-diaminopyrimidine dihydrochloride and 1 g of 4-dimethylamino pyridine. After stirring for at first 2 hours at room termperature and then for 1.5 hours at 100° C., the reaction mixture was evaporated to dryness, mixed with water, and neutralized with sodium bicarbonate. The precipitate obtained was used in the next step without further purification.

Yield: 5.4 g (65% of theory),
M.p.: 188° C.

(b)

8-(4-Chloro-2-methoxy-phenyl)-purine-hydrochloride

Three grams of the product obtained according to Example 7(a) were refluxed in 50 ml of phosphorus oxychloride for four hours. The reaction mixture was evaporated almost to dryness and then poured on water. The precipitate was converted into the hydrochloride by taking it up in ethanol and then mixing it with etheral hydrochloric acid.

Yield: 0.7 g (22% of theory),
M.p.: 243°–245° C. (decomposition, from ethanol).

Example 8

8-(3,4-Dimethoxy-phenyl)-purine

An amount of 7.5 g of 4-amino-5-(3,4-dimethoxy-benzoylamino)-pyrimidine was refluxed in 100 ml of phosphorus oxychloride for six hours. After evaporation and pouring on water, the solution was neutralized by means of potassium carbonate. The solution was evaporated to dryness, and the residue was extracted with boiling ethanol. The alcoholic solution was evaporated, and the remaining product was purified over silicagel (eluate: methylene chloride/ethanol in a volume ratio of 19:1).

Yield: 1.0 g (14% of theory),
M.p.: 241°–243° C.

Example 9

8-(2-Methoxy-4-methylsulfinyl-phenyl)-purine

An amount of 2.27 g of 8-(2-methoxy-4-methylmercaptophenyl)-purine was dissolved in 20 ml of trifluoro acetic acid, and 1.2 ml of 30% hydrogen peroxide were added under cooling to 5° C. After stirring for 3 hours at room temperature and for 0.5 hours at 30° C., the reaction mixture was diluted with water and neutralized with potassium carbonate, and the residue obtained after evaporation was extracted with hot ethanol. The product obtained was purified over silicagel (eluate: methylene chloride/ethanol in a volume ratio of 19:1).

Yield: 1.5 g (65% of theory),
M.p.: 234°–236° C.

Example 10

8-(2-Methoxy-4-methylsulfonyl-phenyl)-purine

In accordance with a procedure analogous to that of Example 9, the above compound was prepared from 2.27 g of 8-(2-methoxy-4-methylmercapto-phenyl)-purine with double the amount of hydrogen peroxide.

Yield: 1.1 g (45% of theory),
M.p.: 244°–246° C. (decomp.).

Example 11

8-(2-Ethoxy-4-methoxy-phenyl)-purine (a)

4-Amino-5-(2-ethoxy-2-methoxy-benzoylamino)-pyrimidine

An amount of 4.4 g of 4,5-diamino-pyrimidine-hydrochloride was dissolved in 50 ml of absolute pyridine. After addition of 7.1 g of 2-ethoxy-4-methoxy-benzoyl-chloride and 1 g of 4-dimethylamino-pyridine, the reaction mixture was at first stirred for three hours at room temperature and then for a further three hours heated at 60° C. After evaporation of the reaction mixture in vacuo, the residue was extracted twice with acetone and subsequently taken up with methanolic hydrochloric acid and filtered over activated charcoal. The filtrate was evaporated, stirred with methanolic ammonia, and, after renewed evaporation, purified by chromatography on silicagel (eluate: methylene chloride/ethanol in a volume ratio of from 100:0 to 97:3).

Yield: 2.3 g (27% of theory),
M.p.: 170°–173° C.

(b) 8-(2-Ethoxy-4-methoxy-phenyl)-purine

An amount of 2.3 g of 4-amino-5-(2-ethoxy-4-methoxybenzoylamino)-pyrimidine was refluxed in 20 ml of phosphorus oxychloride for 2.5 hours. The reaction mixture was poured on ice, and the solid product formed was filtered off. The filtrate was made alkaline by means of sodium bicarbonate and extracted with ethyl acetate. After evaporation of the ethyl acetate phases, the residue was combined with the solid product obtained above and purified by chromatography on silicagel (eluate: methylene chloride/ethanol in volume ratio of from 100:0 to 97:3).

Yield: 0.6 g (28% of theory),
M.p.: 178°–180° C.

Example 12

8-(2-n-Propyloxy-4-methoxy-phenyl)-purine-hydrochloride (a)
4-Amino-5-(2-n-propyloxy-4-methoxy-benzoylamino)-pyrimidine The above compound was prepared from 4.4 g of 4,5-diaminopyrimidine hydrochloride and 7.6 g of 2-n-propyloxy-4-methoxy-benzoylchloride using a procedure analogous to that of Example 11(a). The crude product obtained was used in the next step without further purification.

(b)
8-(2-n-Propyloxy-4-methoxy-phenyl)-purine-hydrochloride

In accordance with a procedure analogous to that of Example 11(b), the above compound was prepared from 4.1 g of the crude product obtained according to Example 12(a). The hydrochloride was precipitated from acetone by means of ethereal hydrochloric acid.

Yield: 1.0 g (23% of theory),
M.p.: 221°–222° C. (decomp.).

Example 13

8-(2-Ethoxy-4-methylmercapto-phenyl)-purine-hydrochloride

Three grams of 2-ethoxy-4-methylmercapto-benzoic acid and 2.2 g of 4,5-diamino-pyrimidine hydrochloride were refluxed in 30 ml of phosphorus oxychloride for three hours. The reaction mixture was poured on ice and then made ammoniacal, and the supernatant solution was decanted from the semicrystalline residue. After dissolution in methanol and filtering off from the insoluble products, the residue was purified over a silicagel column (eluate: methylene chloride/ethanol in volume ratio of from 100:0 to 98:2). The hydrochloride was precipitated from acetone with ethereal hydrochloric acid.

Yield: 1.1 g (24% of theory),
M.p.: 231°–235° C. (decomp.).

Example 14

8-(2-Ethoxy-4-methylsulfinyl-phenyl)-purine-hydrochloride and 8-(2-Ethoxy-4-methylsulfonyl-phenyl)-purine-hydrochloride An amount of 0.9 g of 8-(2-ethoxy-4-methylmercaptophenyl)-purine hydrochloride was dissolved in 10 ml of trifluoro acetic acid at 5° C., 0.35 ml of 30% hydrogen peroxide were added, and the mixture was stirred for one hour. After dilution with water, the reaction mixture was made alkaline by means of potassium carbonate and evaporated in vacuo. The residue was extracted with absolute ethanol. The evaporation residue of the alcoholic solution was chromatographed on silicagel. During elution with methylene chloride/ethanol (volume ratio of from 100:0 to 95:5), at first the sulfone and subsequently the sulfoxide were obtained. The respective hydrochlorides were precipitated from acetone by means of ethereal hydrochloric acid.

Yield: 0.15 g (15% of theory) of 8-(2-ethoxy-4-methylsulfonyl-phenyl)-purine hydrochloride of m.p.: 173°–174° C. and 0.19 g (19% of theory) of 8-(2-ethoxy-4-methylsulfinyl-phenyl)-purine hydrochloride of m.p.: 220°–221° C. (decomp.).

The following examples are intended to illustrate the production of some pharmaceutical preparations:

Example 15

Tablets containing 100 mg of
8-(2-Methoxy-4-methylsulfinylphenyl)-purine

Composition of one tablet:

| Component | Amount (mg) |
|---|---|
| Active ingredient | 100.0 |
| Lactose | 50.0 |
| Polyvinyl pyrrolidone | 5.0 |
| Carboxy methyl cellulose | 19.0 |
| Magnesium stearate | 1.0 |
| | 175.0 |

Method of preparation

The active ingredient, the lactose, and a small amount of water were admixed, and the moist admixture was granulated through a screen of mesh size 1.5 mm. The granulate was dried in a circulation air drier at 50° C., granulated through a screen of mesh size 1.0 mm, mixed with polyvinyl pyrrolidone, carboxy methyl cellulose, and magnesium stearate, and pressed into tablets.

| Weight of tablets: | 175 mg |
|---|---|
| Punch: | 8 mm φ |

Example 16

Coated Tablets containing 50 mg of
8-(2-Methoxy-4-methylsulfinyl-phenyl)-purine

Composition of one tablet core:

| Component | Amount (mg) |
|---|---|
| Active ingredient | 50.0 |
| Corn starch dried | 20.0 |
| Soluble starch | 2.0 |
| Carboxymethyl cellulose | 7.0 |
| Magnesium stearate | 1.0 |
| | 80.0 |

Method of preparation

The active ingredient and the corn starch were homogeneously moistened with an aqueous solution of the soluble starch to form a moist admixture. The moist admixture was granulated through a screen of mesh size 1.0 mm, and the resulting granulate was dried in a circulation air drier at 50° C. Dried granulate was granulated through a screen of mesh size 1.0 mm, mixed with the remaining auxiliary components, and pressed into tablet cores.

| Weight of core: | 80 | mg |
|---|---|---|
| Punch: | 6 | mm |
| Radius of curvature: | 5 | mm |

The tablet cores were covered with a sugar coating in conventional manner. The finished coated tablets were polished by means of bees wax.

Weight of coated tablets: 120 mg.

Example 17

Suppositories containing 75 mg of
8-(2-methoxy-4-methylsulfinyl-phenyl)-purine

Composition of one suppository:

| Component | Amount (mg) |
|---|---|
| Active ingredient | 75.0 |
| Suppository mass (e.g., Witepsol H 19 ® or Witepsol W 45 ®, available from Fa. Chemische Werke Witten GmbH) | 1625.0 |
| | 1700.0 |

Method of preparation

The suppository mass was melted. At 38° C. the pulverized active ingredient was homogeneously dispersed in the melt. The mass was cooled to 35° C. and poured into slightly pre-cooled suppository molds.

Weight of supositories: 1.70 g

Example 18

Ampules containing 50 mg of
8-(2-Methoxy-4-methylsulfinylphenyl)-purine

One ampule contains:

| Component | Amount |
|---|---|
| Active ingredient | 50.0 mg |
| Sorbitol | 250.0 mg |
| Water (distilled) to | 5.0 ml |

Method of preparation

The active ingredient and the sorbitol were dissolved in distilled water, and the mixture obtained was made up to the given volume and filtered sterile.

| Filling: | into 5 ml ampules |
| Sterilization: | 20 minutes at 120° C. |

Example 19

Drop solution containing 250 mg of
8-(2-Methoxy-4-methylsulfinyl-phenyl)-purine per 5 ml Composition of 100 ml of solution:

| Component | Amount |
| --- | --- |
| Active ingredient | 5.0 g |
| Methyl p-hydroxybenzoate | 0.035 g |
| Propyl p-hydroxybenzoate | 0.015 g |
| Aniseed oil | 0.05 g |
| Menthol | 0.06 g |
| Saccharin sodium | 1.0 g |
| Glycerin | 10.0 g |
| Ethanol | 40.0 g |
| Water (distilled) to | 100.0 ml |

Method of preparation

The benzoates were dissolved in ethanol, and the aniseed oil and menthol were added thereto. Subsequently, the active ingredient, glycerin, and saccharine sodium were dissolved in water, and the solution obtained was added to the first solution. The combined solutions were filtered sterile.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A compound of the formula

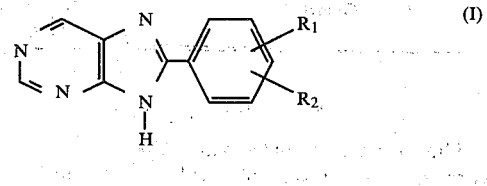

(I)

wherein
$R_1$ is a halogen atom; an alkoxy group of from 1 to 3 carbon atoms, the alkoxy group being optionally substituted by an alkylmercapto, alkylsulfinyl, or alkylsulfonyl group, the alkyl moiety thereof having from 1 to 3 carbon atoms; or an alkylmercapto, alkylsulfinyl, or alkylsulfonyl group, wherein the alkyl moiety has from 1 to 3 carbon atoms, and $R_2$ is an alkoxy group of from 1 to 3 carbon atoms, or a pharmacologically acceptable acid addition salt thereof.

2. A compound of claim 1, wherein
$R_1$ is chlorine atom or a methoxy, methylmercapto, methylsulfinyl, methylsulfonyl, 2-methylmercaptoethoxy, or 2-methylsulfinylethoxy group, and
$R_2$ is a methoxy, ethoxy, or propoxy group, or a pharmacologically acceptable acid addition salt thereof.

3. A compound of claim 2, wherein the radicals $R_1$ and $R_2$ are present in the 2-, 3- and/or 4-position of the phenyl moiety.

4. The compound of claim 1, which is 8-(2,4-dimethoxyphenyl)-purine or an acid addition salt thereof.

5. The compound of claim 1, which is 8-(2-methoxy-4-methylmercapto-phenyl)-purine or an acid addition salt thereof.

6. The compound of claim 1, which is 8-(2-methoxy-4-methylsulfinyl-phenyl)-purine or an acid addition salt thereof.

7. The compound of claim 1, which is 8-[4-methoxy-2-(2-methylsulfinyl-ethoxy)-phenyl]purine or an acid addition salt thereof.

8. A method of increasing muscular contraction in a host which comprises administering an effective amount of a pharmaceutical composition of claim 1.

9. A method of treatment of chronic cardiac insufficiency or cardiogenic shock which comprises administering to a host an effective amount of a pharmaceutical composition of claim 8.

10. A pharmaceutical composition having a positive inotropic activity in a non-chemical manner which comprises an effective amount of a compound of the formula

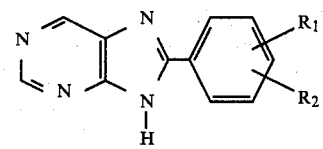

wherein
$R_1$ is a hydrogen or halogen atom; an alkoxy group of from 1 to 3 carbon atoms, the alkoxy group being optionally substituted by an alkylmercapto, alkylsulfinyl, or alkylsulfonyl group, the alkyl moiety thereof having from 1 to 3 carbon atoms; or an alkylmercapto, alkylsulfinyl, or alkylsulfonyl group, wherein the alkyl moiety has from 1 to 3 carbon atoms, and
$R_2$ is an alkoxy group of from 1 to 3 carbon atoms, or a pharmacologically acceptable acid addition salt thereof, and one or more pharmaceutically acceptable carriers and/or diluents.

* * * * *